United States Patent [19]

Tosaki

[11] Patent Number: 4,829,830
[45] Date of Patent: May 16, 1989

[54] APPARATUS FOR MEASURING VISCOELASTICITY

[75] Inventor: Chikao Tosaki, Chuo, Japan

[73] Assignee: Japan Synthetic Rubber Co., Ltd., Tokyo, Japan

[21] Appl. No.: 183,238

[22] Filed: Apr. 19, 1988

[30] Foreign Application Priority Data

Apr. 25, 1987 [JP] Japan ................................ 62-101143

[51] Int. Cl.$^4$ ............................................. G01N 3/22
[52] U.S. Cl. .......................................... 73/847; 374/48
[58] Field of Search ............................ 73/847, 848, 60; 374/47, 48

[56] References Cited

U.S. PATENT DOCUMENTS 3,479,858 11/1969 Umeno et al. ......................... 374/48
3,720,099 3/1973 Wolff et al. ............................ 73/847

OTHER PUBLICATIONS

International Standard ISO 6502–Ref. No. ISO 6502-1983(E) Dec. 15, 1983.
International Standard ISO 3417–Ref. No. 3417-1977(E) Feb. 1, 1977.
Japanese Publication 3105–1980–Measurement of Curing Characteristics with Oscillating Type Curemeter.

Primary Examiner—Jerry W. Myracle
Attorney, Agent, or Firm—Oliff & Berridge

[57] ABSTRACT

In an apparatus for measuring viscoelasticity, dies are provided in their working face with a plurality of grooves arranged in a radial pattern, each groove cut to increase in width toward the periphery of the die face. Because of this groove design, air bubbles are unlikely to remain in the specimen. In addition, the specimen is far much less likely to slip between the opposed die faces in rotational oscillation generated therein for purposes of measurement, so that reduction in oscillatory angle, lessening of torque and friction disturbances that might otherwise occur as a result of slippage, are prevented. Since the shearing stresses generated in the specimen are transmitted to a torque detection die accurately as torques, precise detection of torque as a function of the viscoelastic stress in the specimen becomes possible.

9 Claims, 11 Drawing Sheets

APPARATUS FOR MEASURING VISCOELASTICITY

BACKGROUND OF THE INVENTION

1. FIELD OF THE INVENTION

The present invention relates to an apparatus for measuring viscoelasticity and, in particular to such an apparatus capable of tracing the change in viscoelasticity of vulcanized rubbers and thermosetting resins as they are cured.

2. DESCRIPTION OF THE PRIOR ART

Viscoelasticity testing is carried out to detect whether or not vulcanized rubbers and thermosetting resins have the designed physical properties after unvulcanized stock is subjected to vulcanizing processes or thermosetting resins are subjected to thermosetting processes. As for a rubber, ISO-3417-1977 "Rubber-Measurement of Vulcanization Characteristics with the Oscillating Disc Curemeter" and The Japan Rubber Manufacturers Association Standard SRIS 3105-1980 "Measurement of Curing Characteristics with Oscillating Type Curemeter" prescribe methods for testing viscoelasticity.

FIG. 1 is a view showing a model example of a conventional apparatus for measuring viscoelasticity employing an SRIS 3105-1980 B-type die.

In FIG. 1, an upper die 1 (or the die for torque detection) as grooved in its working lower face a lattice pattern. An upper stationary die 3 (the stationary die on the torque detection side) is mounted enclosing the upper die 1 via an upper ring seal 5 (the seal on the torque detection side). The upper die 1, the upper stationary die 3 and the upper seal 5 constitute an upper die assembly B.

A lower die 2 (the driving die) also is provided in its upper working face with grooves of a lattice pattern and is surrounded by a lower stationary die 4 (the stationary die on the drive side) via a lower ring seal 6 (the seal on the drive side). The lower die 2, the lower stationary die 4 and the lower seal 6 constitute a lower die assembly A.

The lower die 2 is mounted on top of a drive shaft 8 in which a heating element 20 is embedded. The drive shaft 8 is connected to a drive mechanism which may consist of a motor 10, an eccentric motor drive shaft 11, and a crank arm 12. The upper die 1 is mounted on a torque detection shaft 7 in which a heating element 19 is embedded. The torque detection shaft 7 is provided with a torque arm 13 which is connected to a load cell 14.

The upper die assembly B includes a heating plate 15 having a heating element 21 to heat the heating plate and is supported by an upper base 17. Also, the lower die assembly A includes a heating plate 16 having a heating element 22 to heat the heating plate and is supported by a lower base 18. A pneumatic cylinder 23 is connected to the upper base 17 to pneumatically drive the latter in vertical direction.

The apparatus of FIG. 1 may be operated in the following steps for measurement of viscoelasticity.

(1) First, the pneumatic cylinder 23 is actuated to pull upward the upper base 17 to lift the upper die assembly B away from the lower die assembly A. Then, a specimen of unvulcanized stock, hereinafter referred to as simply "rubber specimen", is placed on the working surface of the lower die 2 of the die assembly A.

(2) The pneumatic cylinder 23 is restored to lower the upper base 17 until the upper die 1 is pressed against the lower die 2, with the rubber specimen being packed within a specimen chamber 26 which is the sealed cavity formed between the die assemblies A and B.

(3) While the heating elements 19, 20, 21 and 22 keep the rubber specimen at a predetermined temperature the lower die 2 is rotationally oscillated by the drive mechanism so that the oscillating force is applied to the rubber specimen. The torque mediated by the rubber specimen is transmitted to the upper die 1 and detected by load cell 14.

In this manner, the change in the curing degree of the rubber specimen is measured as a function of time. Extra portions of the rubber specimen are ejected out onto a flash channel 24.

FIG. 2 is an enlarged cross-sectional view of a die assembly which meets the prescriptions of SRIS 3105-1980. The die assembly is substantially similar in construction to FIG. 1, and like components are indicated by like reference numerals, except for numerals 27 and 28 designated means for measuring temperature, respectively.

In those prior apparatuses, to secure an exact torque transmission, in the working surfaces of the dies, and those of disc, which will later be described, grooves are cut to prevent slip of the rubber specimen. Despite these devices, those conventional apparatuses have suffered the disadvantage of failing in effective torque transmission.

FIGS. 3A and 3B are partial plan and cross-sectional views, respectively, of an upper or a lower die for showing grooves 31 which meet the prescriptions of SRIS 3105-1980 type B die. Each of the grooves 31 is cut to a width of 1 mm and a depth to 0.5 mm. Because of the lattice pattern (or check pattern) of the grooves 31 which are not cut in the same directions as the flow of filled rubber specimen, the grooves have tended to have air bubbles left retained. These air bubbles affect greatly the precise torque transmission.

Grooves of a die prescribed in ISO-3417-1977 are shown in FIG. 4, and those of a biconical disc prescribed in the same standard are shown in FIGS. A and 5B. The specimen is filled in a sealed cavity formed between the opposed working faces of the upper and lower dies, and in operation is subjected to oscillation by the disc. FIG. 4 is a plan view showing the under surface of the upper die 32. The grooves 33 as depicted in FIG. 4, are arranged in a radial pattern, equally angularly spaced at an angle of 20°, cut to a width of 1.6 mm and a depth of 0.8 mm. The working face of the lower die, not shown, may also be cut to a similar groove pattern and dimensions.

FIGS. 5A and 5B are a top and side view, respectively, of a biconical disc 34 which is inserted in the sealed cavity formed between the working faces of the upper and lower dies and it will oscillate the filled rubber specimen. As illustrated in FIGS. 5A and 5B, in the upper working face of the disc 34 alternating long grooves 35 and short grooves 36 are formed. These grooves are arranged in a radial pattern, equally angularly spaced at an angle of 10°. The width and depth of each of grooves is both 0.8 mm, and the length of long and short grooves are 12.5 mm and 7.5 mm, respectively. Also, the lower working face of the disc 34 is provided with alternating long 9.5 mm and short 7.5 mm grooves, cut to the same width and depth as the upper surface.

SRIS 3105-1980 states the prescription as disc type viscoelasticity tester A similar to ISO-3417-1977 regarding a radial groove pattern. The radial groove pattern, unlike latticed groove pattern, has the advantage that the air bubbles which might possibly mingle with are likely to be released together with the flash, since the grooves are cut in the same directions as the rubber specimen would flow upon filling into the sealed cavity formed between the upper and lower dies. However, in the prior art techniques, the use of these radial grooves has not satisfactory effects in preventing slip, even with specimens relatively hard to slip. This will be discussed in more detail.

FIG. 6 is a partial perspective view of the die or disc provided with radial grooves as shown in FIGS. 4, 5A and 5B, cut along a cylindrical surface having its center at the axis of rotation of the die or disc. The section is shown with emphasizing shade. The character F designates the flat portions between adjacent grooves while G indicating the bottom of each groove. In addition, the character f represents the circumferential dimension of the flat portions F. The breadth of bottoms G is represented by the character g. It then follows that f+g is equivalent to the pitch of the grooves. The ratio $\alpha$ of g to groove pitch (f+g) is defined by the following equation (1):

$$\alpha = g/(f+g) \tag{1}$$

In an apparatus for measuring viscoelasticity, a pair of metal surfaces (for example, an upper and a lower die; or a disc and a die), each surface having grooves cut therein, are opposed at predetermined intervals to form a sealed cavity. The rubber specimen to be tested is filled into the sealed cavity. Then, one of the surfaces is put into rotational oscillation which exerts a shearing stress on the specimen. This shearing stress in the specimen in oscillation is collected as a torque into the central shaft of the detecting surface of the other metal surface. This torque is measured by a load cell or a torque meter which is to bear the rotary force of the shaft. This is the principle of measurement utilizing a torsional oscillating type viscoelasticity measurement apparatus. In this method, as shearing stress generated by the oscillating metal surface increases, the specimen increases its tendency of slipping at the interface with metal. The flat portions F offer no resistance against the slipping, while only the bottoms G in the grooved surfaces prevent the slippage as gripping the specimen. Since the shearing stress generated in the specimen is substantially equal on the flat portions F and on the bottoms G, the shearing stress for each pitch is proportional to (f+g). Also, the force to prevent slippage is proportional to g. Therefore, the ratio of g to (f+g), $\alpha$ defined by equation (1), correlates with the maximum degree for the linear grooves to grip the rubber specimen and prevent its slippage. Accordingly, this ratio a will hereinafter be referred to as "grip ratio".

Conventionally, the grooves having a uniform width, as illustrated in FIGS. 4, 5A and 5B have been employed, as a result the value of $\alpha$, while greater around the center of the dies or discs, tended to become smaller near their periphery. According to the theory of the linear elasticity, the relationship between torque M and effective radius R of a die or disc is:

$$M\alpha R^3 \text{ for the conical plate type} \tag{2}$$

$$M\alpha R^4 \text{ for the parallel disc type} \tag{3}$$

Equations (2) and (3) teach that, in either a die or a disc, the peripheral portions are essential for generating the torque. This means that, unless a proper enough magnitude of $\alpha$ is maintained over the entire surface down to the periphery, it would be difficult to obtain stable reading of true values of shearing stress without slippage disturbances. In conventional measuring devices, $\alpha$ has tended to be a minimum at the periphery which is the most important part, making it difficult altogether to prevent the slippage of specimen. As a concrete example, computation indicates that $\alpha$ is approximately 0.26 at the periphery for each of FIGS. 4, 5A and 5B.

In the prior art, as an experimental auxiliary method for preventing slippage, roughening the working surface of precision machined dies or discs by sand blasting and also making fine unevenness on the flat portions F shown in FIG. 6 is proposed and this method is considered to be effective in preventing the slippage. However, introduction of this method is to admit that the linear grooves, primarily intended for such prevention, fail to serve the very purpose. Furthermore, the roughening of the surface, while temporarily effective in the initial stages of operation, will lose effects in the passage of time since the metal surfaces are increasingly contaminated with specimen. To restore the surfaces, brushing is required, which will in turn wear out the fine unevenness of the surface. Here, it is difficult to maintain reliable measurements throughout time.

As stated above, in the conventional apparatus for measuring viscoelasticity, the slippage between the specimen and the dies or disc occurs easily and it is difficult to obtain accurate torque measurement. With thermosetting resin, in particular, errors of measurement have tended to become even greater because of slippage.

SUMMARY OF THE INVENTION

The present invention is provided to resolve the above problems of the conventional apparatus. The object of the present invention is to provide an apparatus for measuring viscoelasticity which is free from the above problems and is capable of efficient measuring operation.

In the first aspect of the present invention, an apparatus for measuring viscoelasticity in which a specimen to be measured is filled into a specimen chamber provided with at least one stationary surface and at least one driving surface and is torsionally oscillated through the at least one driving surface and a viscoelastic stress generated in the specimen is monitored as a torque through either the at least one stationary surface or the at least one driving surface, comprises:

a plurality of grooves formed in both or either of the at least one stationary surface and the at least one driving surface which are contacted by the specimen when the specimen is filled, the grooves being arranged in a radial pattern and, each cut to increase in circumferential width toward the periphery of the surface.

Here, the grooves may be cut to have the ratio of "g" to the sum of "f" and "g" not less than 0.4, where "f" is the circumferential spacing of the radially arranged grooves and "g" is the circumferential width of each grooves.

The ratio of "g" to the sum of "f" and "g" may be not less than 0.6.

The at least one stationary surface and the at least one driving surface may be the faces of a pair of dies, respectively.

The at least one stationary surface may comprise the opposed faces of a pair of dies while the at least one driving surface may be the face of a biconical disc interposed between the dies.

Each of the paired dies may have a stationary die mounted around them.

One of the paired dies may include an intermediate plate.

In the second aspect of the present invention, an apparatus for measuring viscoelasticity, comprises:
a first die;
a second die opposed to the first die;
a first stationary die mounted around the first die;
a second stationary die mounted around the second die;
an intermediate plate releasably mounted within the second stationary die; and
a plurality of grooves cut in at least one of the opposed faces of the first die and the second die, the grooves being arranged in a radial pattern, each cut to increase in circumferential width toward the periphery of the die face.

In the third aspect of the present invention, an apparatus for measuring viscoelasticity, comprises:
a first die;
a second die opposed to the first die;
a first stationary die mounted around the first die;
a second stationary die mounted around the second die; and
an intermediate plate releasably mounted within the second stationary die.

The above and other objects, effects, features and advantages of the present invention will become more apparent from the following description of preferred embodiments thereof taken in conjunction with the accompanying drawings.

DETAILED DESCRIPTION OF PREFERRED EMBODIMENTS

Preferred embodiments of the present invention will be described in full detail in conjunction with the accompanying drawings.

Figure 8A:
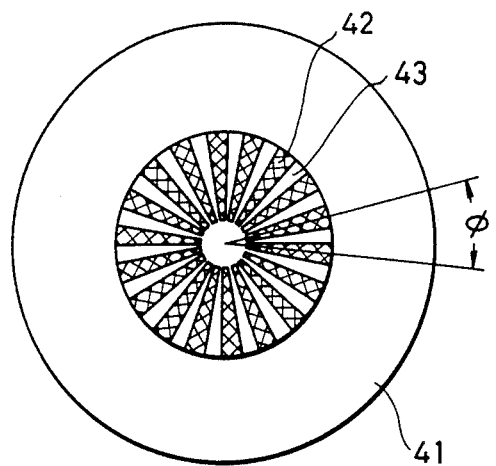
FIGS. 8A and 8B are plan and side views, respectively, of a first embodiment of the die according to the present invention.
Figure 8B:
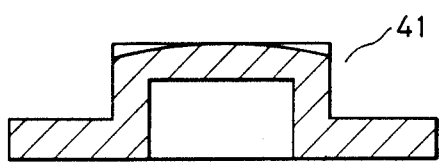

An embodiment of the present invention is shown in FIGS. 8A and 8B. FIG. 8A is a plan view and FIG. 8B is a cross-sectional view of a lower die constructed in accordance with the present invention. The lower die 41 is provided with a plurality of grooves 42, shaded for emphasis, and flat portions 43 in its top working face. In FIG. 8A, the grooves 42 are illustrated with an angular pitch of 20° to help the understanding. But the present invention is not limited to this specific angle.

Figures 9A, 9B:
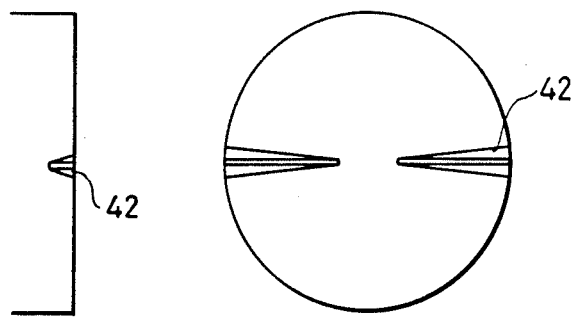
FIGS. 9A and 9B are plan and side views, respectively, of the die showing the shape of a groove.

FIGS. 9A and 9B are enlarged plan and side views of the lower die 41, respectively. To clarify the concept, only two grooves 42 are shown in FIG. 9A whereas one groove 42 in cross-section is depicted in FIG. 9B, making their shape more definite. As shown best in FIGS. 8A and 9A, the grooves 42 are arranged in a radial pattern, each increasing in width toward the periphery of the working face of the die 41. Accordingly, the grip ratio $\alpha$ defined by equation (1) is not decreased at peripheral portions of the die where the torque is principally generated, so that a die pattern preferable to prevent slippage can be realized. The value of $\alpha$ can be specified by the selected shape of the groove 42 cut and may be determined to be uniform along the entire length of the grooves. Alternatively, the value may be determined to become greater toward the periphery of the working face of the die.

In order to exhibit the intended effects of the present invention more conspicuously, it is preferable that both the upper and lower dies have the above-mentioned grooves in their working faces.

There are contrived various methods for cutting such radial grooves pattern as increase in width toward the periphery, as illustrated in FIGS. 8A and 9A. In one method, groove patterns can be copied from a mother mold by precision casting or electrical discharge machining. In an alternative method, a pattern may be cut in single operation by the numerically controlled milling machine. One of the relatively simpler methods for cutting grooves with enhanced precision and with greater efficiency will be described.

Figure 10:
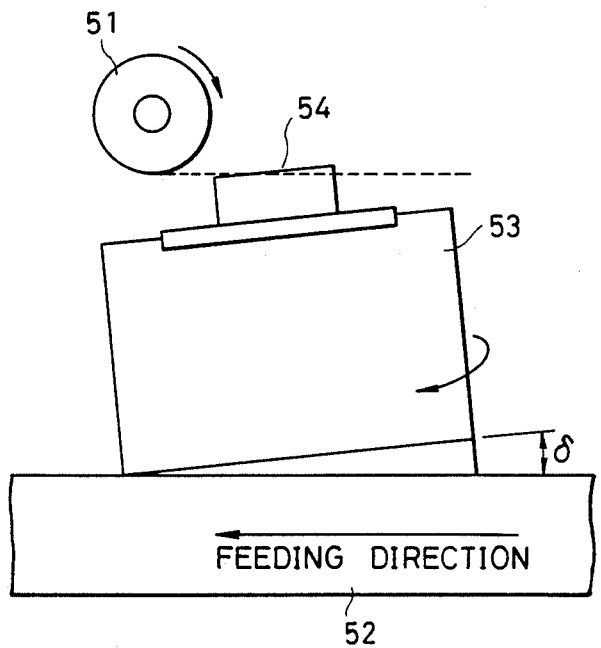
FIG. 10 is a view of a milling machine in operation, showing how the grooves are formed.
Figures 11, 12, 13:
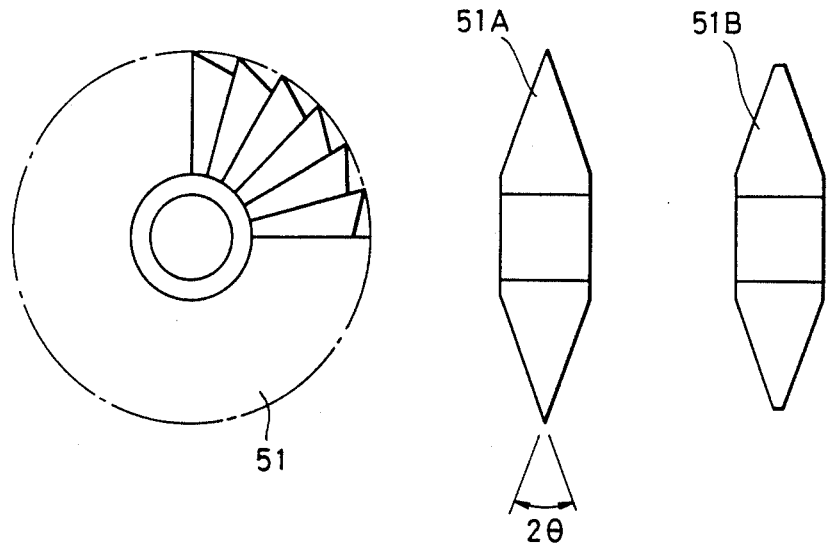
FIG. 11 is a plan view of a cutter.
FIGS. 12 and 13 are cross-sectional views of a cutter, respectively.

FIG. 10 is a schematic view of an ordinary milling machine with a double angle or equal angle milling cutter 51 employed to cut grooves to a desired pattern. FIG. 11 is a plan enlarged view of the double angle milling cutter 51. Commercially available are double angle cutters which comprise cutting edges 51A with an edge angle of $2\theta$, as depicted in FIG. 12. For the purpose of the present invention the cutter with cutting edge 51A may be used, or such cutting edges may be ground to a blade 51B shown in FIG. 13. Use of a double angle milling cutter with edges shaped as illustrated in FIG. 13 would leave a small flat circle uncut in the center of the die 41. However, if this flat circle was small enough, its effect on measured data would be almost negligible since the torque at the center would be extremely insignificant for measurement, as will be clear from equations (2) and (3) above. It is very easy to have this flat circular portion as small in dimension as possible. Furthermore, a small flat portion left in the center of the working surface of the die 41 would offer the advantage that measuring the thickness of cured specimen can be done with increased ease.

As shown in FIG. 10, in groove cutting, the milling machine is operated with the die 54 to be grooved placed on a rotary index head 53 which is set on the table 52. Constant grip ratio $\alpha$ along the entire groove length can be obtained by selecting the angle $\delta$ by which the rotary index head 53 is tilted. This angle $\delta$ is related to grip ratio $\alpha$, edge angle $\theta$ and pitch angle $\phi$ of radially arranged grooves in the following equation:

$$\delta = \alpha\phi/2 \tan \theta \qquad (4)$$

The above descriptions are given for the cutting of grooves in a die having a flat head or in a flat circular disc according to the present invention. When cutting similar grooves in a conical die or disc, the rotary index head is tilted for an extra angle in line with the conical angle of the die or disc.

The higher precision than obtainable with a milling machine with a double angle milling cutter as explained in connection with FIG. 10, would be achieved by using a grinding stone whose head is cut to a cross section as shown in FIG. 12 or FIG. 13 in conjunction with a surface grinder.

To secure the prevention of specimen slippage in viscoelasticity measurement, grip ratio $\alpha$ may preferably be selected in the range of from 0.4 to 0.9 for rubber specimens which are less likely to cause a slip, and in the range of from 0.4 to 0.9, more preferably, from 0.6 to 0.9 for resin specimens which are more likely to slip. In addition, it is preferable to have the spacings of the radial grooves or flat portions at the peripheral portion of the die, not greater than the distance between the upper and lower dies at the moment they are aligned for the measurement, for example, 2 mm for SRIS 3105-1980 type B die. Furthermore, the width of the grooves is preferably determined in relation to two parameters of grip ratio $\alpha$ and the width of the flat portions. Groove depth is preferably in the range of from ½ to 2 times groove width. Below this range, specimen is more likely to slip. Above it, removal of specimen become somewhat difficult after measurement.

Figure 1:
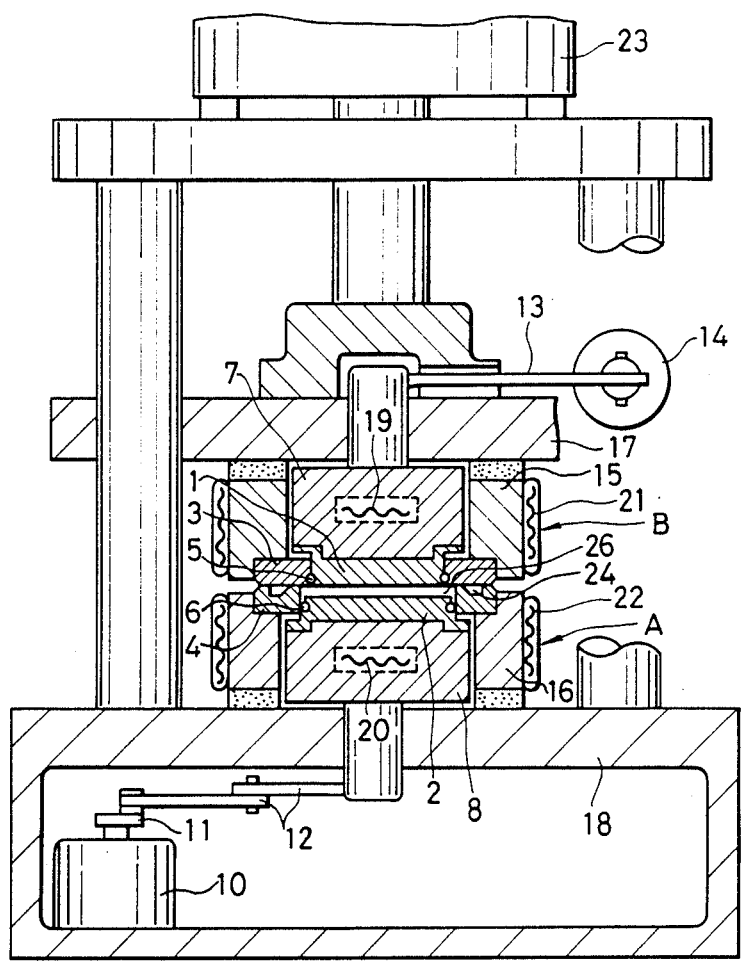
FIG. 1 is a schematic view of a conventional apparatus for measuring viscoelasticity.
Figure 14:
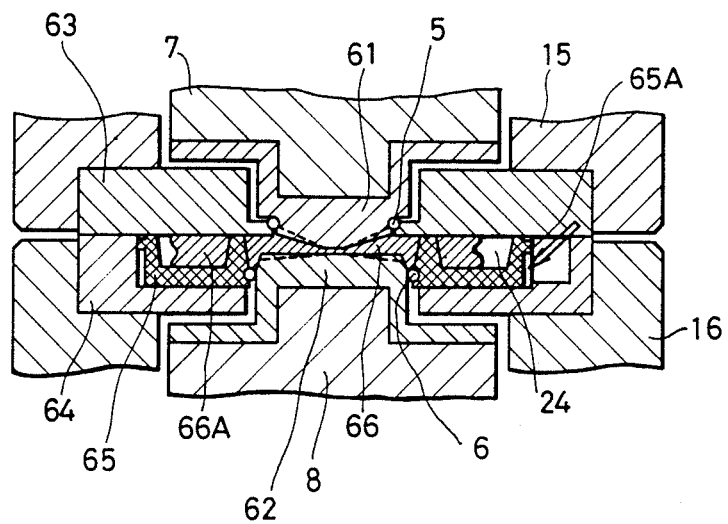
FIG. 14 is a partial cross-sectional view of an apparatus for measuring viscoelasticity having dies similar to the one shown in FIG. 8A.

FIG. 14 is a cross-sectional view of an embodiment of the present invention applied to the SRIS 3105-1980 type B dies. In the figure, an upper die 61 is provided with grooves which have a uniform grip ratio $\alpha$ along the entire length of the grooves from center to periphery. Also, a lower die 62 is provided with grooves which are cut to the same pattern as the upper die 61. The upper die 61 is enclosed in an upper stationary die 63, also the lower die 62 is enclosed in a lower stationary die 64. An intermediate plate 65 is disposed in the lower stationary die 64. Specimen 66 is shown between the upper and lower dies, with flash 66A coming out onto a flash channel 24. Other components are designated by like reference numerals as used in FIGS. 1 and 2.

Figure 2:
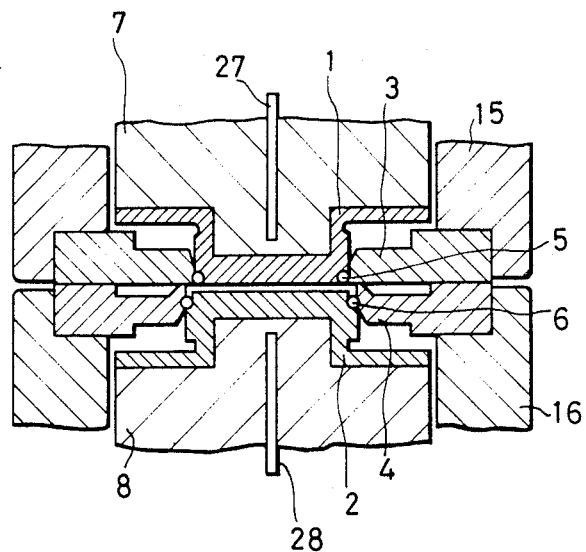
FIG. 2 is a partial enlarged cross-sectional view of another conventional apparatus for measuring viscoelasticity.
Figure 4:
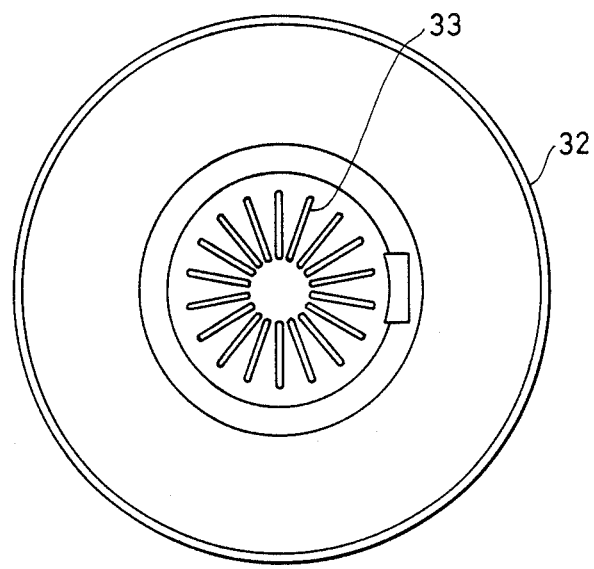
FIG. 4 is a plan view of a conventional die showing radial grooves.
Figure 3A:
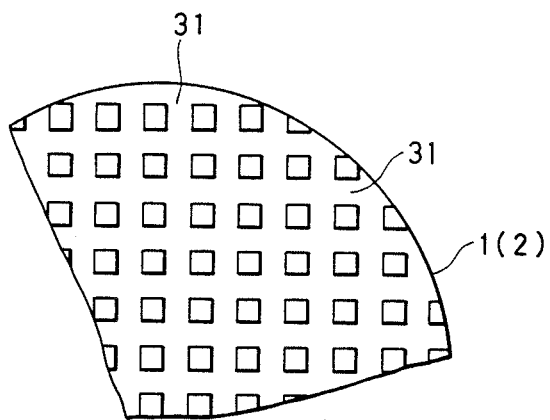
FIGS. 3A and 3B are partial plan and cross-sectional views, respectively, of a latticed groove pattern for conventional dies.
Figure 3B:
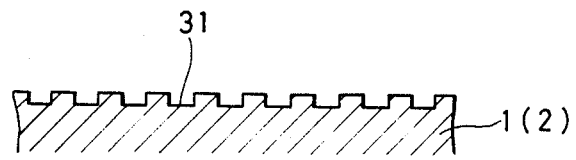
Figure 5A:
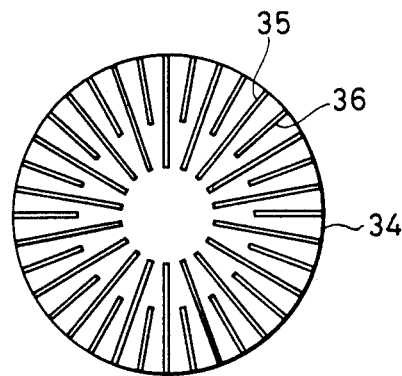
FIGS. 5A and 5B are plan and side views, respectively, of a conventional disc showing radial grooves.
Figure 5B:
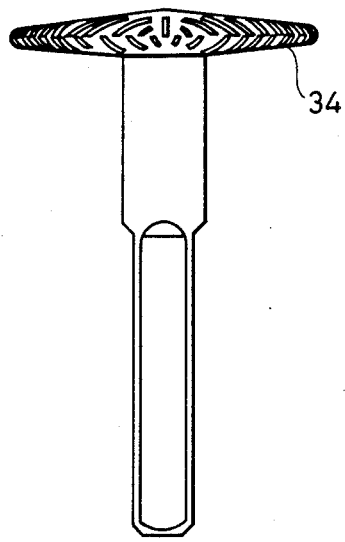
Figure 6:
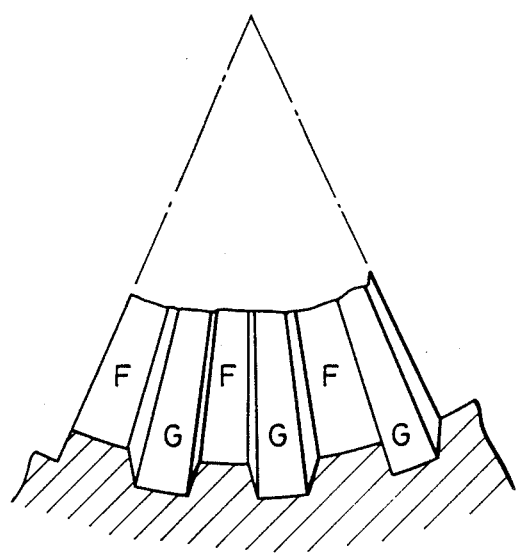
FIGS. 6 and 7 are perspective and cross-sectional views, respectively, showing the shape of a radial groove pattern for a conventional die or disc.
Figure 7:
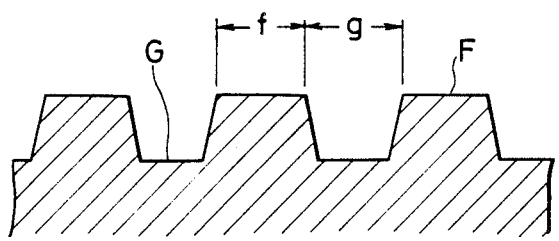
Figure 15:
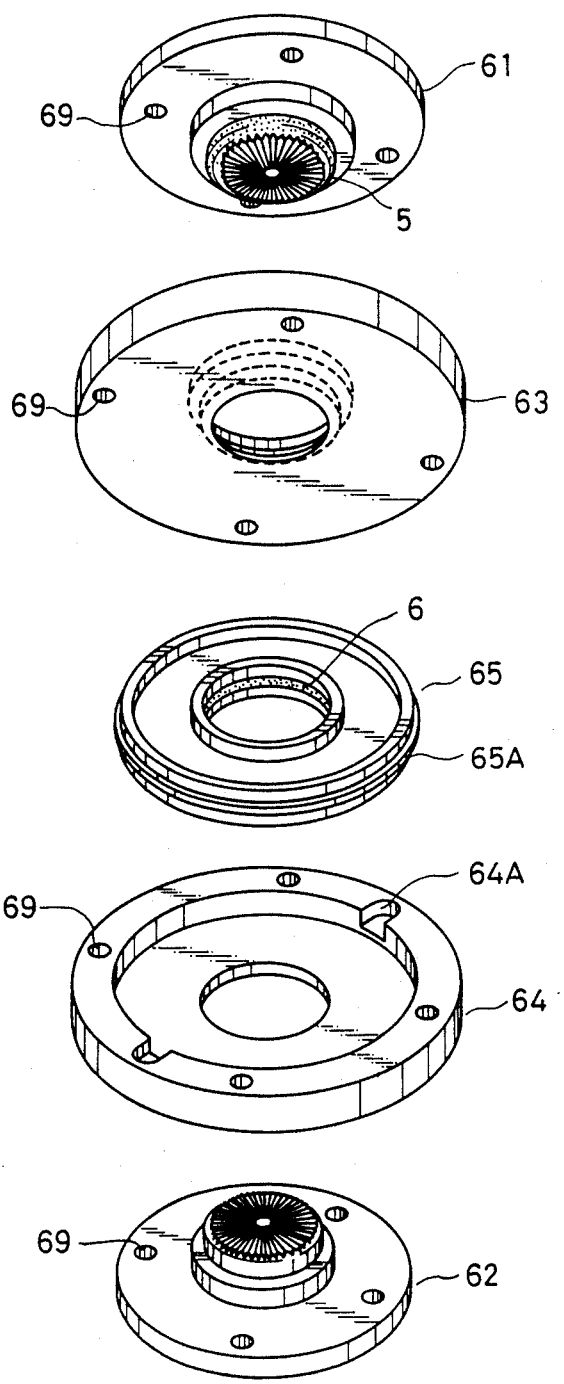
FIG. 15 is an exploded perspective view of the dies showing in FIG. 14.

FIG. 15 is an exploded, perspective view of the dies of FIG. 14. In conventional dies as illustrated in FIG. 2, the head of the upper die is held coplanar with the upper stationary die. In this particular embodiment, the upper die 61 is of a conical shape, with the top of the upper die cone being assembled to protrude farther downward than the bottom surface of the upper stationary die 63. When the viscoelasticity of liquid specimen with a very low viscosity is measured, this projecting top portion of the cone has a large volume to submerge into the liquid specimen, when the dies are closed, enough to allow the specimen to spread and fill the sealed cavity (specimen chamber). In the figure, the numeral 69 designates a counterbore for a fixing screw.

Figure 16:
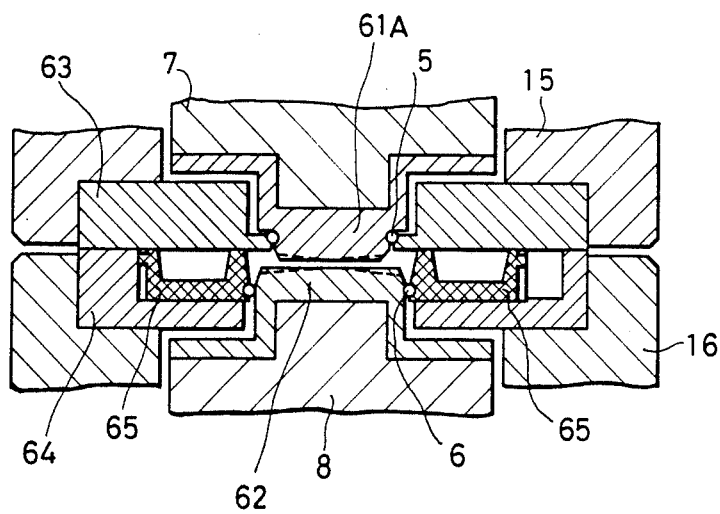
FIG. 16 is a cross-sectional view of dies according to a second embodiment of the present invention.

FIG. 16 is a cross-sectional view of another embodiment of dies assembly according to the present invention. This assembly has an upper die 61, and a lower die 62 both shaped like a flat disc, with a flat head, constructed in accordance with the present invention. As shown, the upper die 61A has its working face held below the plane of the lower stationary die 64, when the upper and lower dies are closed. This arrangement also is designed to produce the same effect as the upper die 61 having a conical working face of FIG. 14.

Referring again to FIG. 14 or 16, the specimen is filled within the cavity defined by the lower die 62 and the intermediate plate 65, then the upper die assembly is pressed to the lower die by means of a pneumatic cylinder, not shown. The measuring portions or upper and lower dies assemblies come closer immediately if the specimen is liquid, or slowly with the increasing temperature and melting of the specimen if it is solid as a pellet or powder, then the upper stationary die 63 and the intermediate plate 65 tightly contact each other, so that the specimen chamber (the above-mentioned cavity) is sealed by a pair of upper and lower seals. The excess of the specimen, along with any volume increase by thermal expansion, is forced out as flash under high pressure developed in the sealed cavity onto a flash channel 24 installed on top of the intermediate plate 65. Since the flash naturally flows out in a radial direction, it can take a smooth flow along the radial grooves without being blocked at all, so that air bubbles are unlikely to remain in the specimen.

After closing the measuring portion, drive means, not shown, is energized to put the drive shaft into rotational oscillation which in turn give the lower die 62 rotational oscillation with a constant small amplitude and with a constant angular frequency so that shearing stress is generated in the specimen. This shearing stress is converted into a torque, when transmitted to the upper die 61 (or 61A), and the torque is measured by a torque meter, not shown, which is connected to the shaft of the upper die. Slippage between the specimen and the contacted face of the upper die 61 (or 61A) as well as between the specimen and the contacted face of the lower die 62 is effectively minimized by radial grooves with a grip ratio as described in detail above, formed in each of the working faces of the dies 61 (or 61A) and 62. With this arrangement, more accurate measurement of viscoelasticity can be achieved by determination of torque as a function of viscoelastic stress generated in the specimen.

Figure 17:
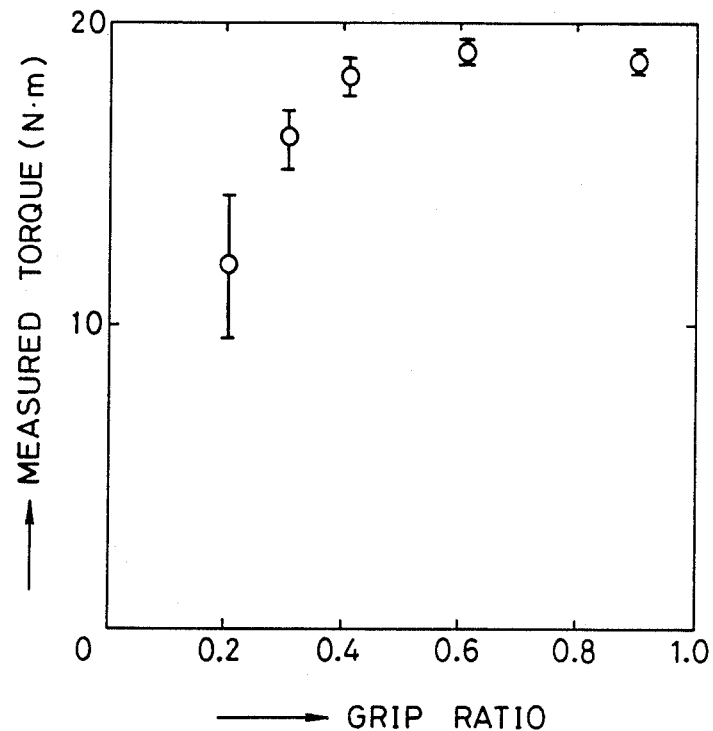
FIG. 17 is a chart showing the relationship between grip ratio and torque in the process of curing.

FIG. 17 illustrates the dependence of the measured torque and its dispersion (or standard deviation) on the grip ratio in viscoelasticity measurement of thermosetting resins (unsaturated polyester resins). As shown in the diagram, torque is small, but greater in dispersion, where grip ratio $\alpha$ is small. On the other hand, where grip ratio α rises, torque becomes more stable in a higher range, with less dispersion.

Figure 18:
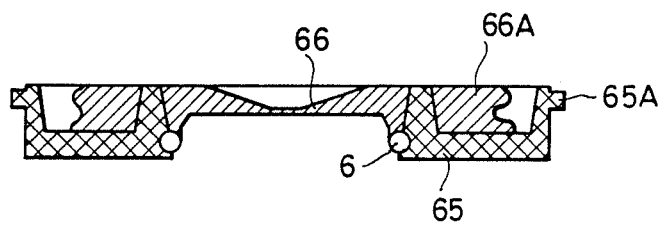
FIG. 18 is a cross-sectional view of specimen after measurement.

When the upper die assembly is lifted up at the end of measurement, in most cases, the upper die assembly is released from the upper die assembly at the boundaries between the cured specimen and the upper die and between the flash and the upper stationary die, the cured specimen, along with the flash, remains in the lower die assembly. Referring back to FIG. 14, when the intermediate plate 65 is raised by applying a lever inserted through a cutout 64A (as indicated by the white arrow in the figure) to the collar 65A and prying it up fulcruming a proper point along the edge of the cutout, the cured specimen, along with the intermediate plate 65, the lower seal 6 and the flash 66A, comes off loose from the lower stationary die, as illustrated in FIG. 18.

The magnitude of the force required to get the specimen loose has nothing to do with the hardness of the specimen, but is closely related with its adhesive force. Thus, with specimen with less adhesive force, smaller force would suffice to separate the specimen. In the case of specimen having much greater adhesive force, the cured specimen combined with the intermediate plate can be separated easily and rapidly from the lower stationary die by coating the upper and lower dies with a mold release agent in advance.

Once the specimen adhered integrally with the intermediate plate is separated from the die assembly, the next job is to remove the specimen and the flash from the surface of the intermediate plate. This task can be achieved with ease and with convenience in a wider place, away from the measuring apparatus. In order to make this removal easy, it is preferable to form draft tapers in the cylindrical surfaces of the intermediate plate, there the specimen and the flash contact it.

After the removal of the specimen is completed, the released intermediate plate and the lower seal are reinstalled into the lower die assembly, and may, after they are heated up to operating temperature, be restarted for subsequent measurement. As outlined above, since this specimen removal can generally be achieved in a very short time, the decrease in temperature of intermediate plate is relatively small. In addition, in most cases, an intermediate plate having a far much lower heat capacity than the rest of the die assembly components may be employed, so that deviation from thermal equilibrium due to the reinstallation of the intermediate plate which has just cooled off, can be minimized, and equilibrium can be recovered rapidly. In this manner, to ease the removal of the specimen by utilizing the intermediate plate means not only an increase in efficiency of measurement, but also saving the time required for the apparatus to wait until proper temperature is reached in high temperature measurement.

Although the above embodiments are described in the application of the present invention to a closed type apparatus having 4 dies (SRIS 3105-1980 type B dies). However, it is to be understood that the present invention should not be limited to it, but also is applicable to semi-closed type apparatus (SRIS 3105-1980 type A die). It is apparent that the aforesaid radial groove pattern in which the grooves are cut so as to offer a uniform grip ratio $\alpha = g/(f+g)$ through the entire length of each groove from center to periphery is applicable to SRIS 3105-1980 type A dies. In addition, if the specimen is rubber, the present invention may also be applicable to other testing apparatus such as ISO-3417-1977 devices and SRIS 3105-1980 disc A type where measurements are taken by giving oscillation to specimen, which is put in the sealed cavity formed by two dies, through a biconical disc being inserted in the sealed cavity, and an apparatus prescribed in ISO-6502-1983 in which a specimen chamber comprises only dies without a disc.

It will easily be seen that in measurement of viscoelasticity air bubbles would be unlikely to remain in the specimen, since grooves arranged in a radial pattern are formed in the die or disc face, each groove cut to increase in width toward the periphery. In addition, because of this groove design, the specimen is far much less likely to slip between the opposed dies or disc face while they are in rotational oscillation, and reduction in oscillatory angle, lessening of torque and friction disturbances which might otherwise occur as a result of slippage, will be prevented. Thus, since the shearing stress generated in the specimen is transmitted to the torque detecting die as the torque accurately, the torque which reflects viscoelastic stress in the specimen can be detected accurately. Furthermore, the use of an intermediate plate will facilitate the separation of the specimen from the die assembly with increased ease after measurement, insuring increased efficiency of operation.

The invention has been described in detail with respect to preferred embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

What is claimed is:

1. An apparatus for measuring viscoelasticity comprising a specimen chamber into which a specimen being analyzed is supplied, said chamber being provided with at least one stationary surface and at least one driving surface; means for torsionally oscillating said specimen through said at least one driving surface; and means for monitoring a viscoelastic stress generated in said specimen as a torque through either said at least one stationary surface or said at least one drive surface, a plurality of grooves being formed in said at least one stationary surface and/or said at least one driving surface, said grooves being contacted by said specimen and being arranged in a radial pattern, said grooves increasing in circumferential width toward a periphery of the surface in which said grooves are formed.

2. An apparatus as claimed in claim 1, wherein said grooves are cut to have the ratio of "g" to the sum of "f" and "g" not less than 0.4, where "f" is the circumferential spacing of said radially arranged grooves and "g" is the circumferential width of each grooves.

3. An apparatus as claimed in claim 2, wherein said ratio of "g" to the sum of "f" and "g" is not less than 0.6.

4. An apparatus as claimed in claim 1, wherein said at least one stationary surface and said at least one driving surface are the faces of a pair of dies, respectively.

5. An apparatus as claimed in claim 4, wherein each of said paired dies has a stationary die mounted around them.

6. An apparatus as claimed in claim 6, wherein one of said paired dies includes an intermediate plate.

7. An apparatus as claimed in claim 1, wherein said at least one stationary surface comprises the opposed faces of a pair of dies while said at least one driving surface is the face of a biconical disc interposed between said dies.

8. An apparatus for measuring viscoelasticity, comprising:
- a first die;
- a second die opposed to said first die, said first and second dies at least partially defining a specimen chamber into which a specimen to be measured is supplied;
- a first stationary die mounted around said first die;
- a second stationary die mounted around said second die;
- an intermediate plate releasably mounted within said second stationary die;
- means for generating viscoelastic stress in said specimen; and
- means for monitoring said viscoelastic stress generated in said specimen,
- a plurality of grooves being formed in at least one of the opposed faces of said first die and said second die, said grooves being arranged in a radial pattern, each cut to increase in circumferential width toward the periphery of the die face.

9. An apparatus for measuring viscoelasticity, comprising:
- a first die;
- a second die opposed to said first die, said first and second dies at least partially defining a specimen chamber into which a specimen to be analyzed is supplied;
- a first stationary die mounted around said first die;
- a second stationary die mounted around said second die;
- an intermediate plate releasably mounted within said second stationary die;
- means for generating viscoelastic stress in said specimens; and
- means for monitoring said viscoelastic stress generated in said specimen.

* * * * *